United States Patent
Cole et al.

(10) Patent No.: US 11,923,096 B2
(45) Date of Patent: Mar. 5, 2024

(54) SYSTEMS AND METHODS FOR INSPECTING A MACHINE

(71) Applicant: HITACHI ENERGY Ltd, Zurich (CH)

(72) Inventors: Gregory Cole, West Hartford, CT (US); William Eakins, Bloomfield, CT (US); Daniel Lasko, East Granby, CT (US); Harshang Shah, Bloomfield, CT (US); Thomas Fuhlbrigge, Ellington, CT (US); Carlos W. Morato, Avon, CT (US); Biao Zhang, West Hartford, CT (US); Luiz Cheim, St. Charles, MO (US); Poorvi Patel, Ballwin, MO (US); Stefan Rakuff, Windsor, CT (US); Saumya Sharma, Enfield, CT (US); Nolan W. Nicholas, Granby, CT (US); Gregory F. Rossano, Enfield, CT (US); Sanguen Choi, Simsbury, CT (US)

(73) Assignee: Hitachi Energy Ltd, Zurich (CH)

( * ) Notice: Subject to any disclaimer, the term of this patent is extended or adjusted under 35 U.S.C. 154(b) by 828 days.

(21) Appl. No.: 16/434,682

(22) Filed: Jun. 7, 2019

(65) Prior Publication Data
US 2019/0287689 A1    Sep. 19, 2019

Related U.S. Application Data

(63) Continuation of application No. PCT/IB2017/001628, filed on Dec. 6, 2017.
(Continued)

(51) Int. Cl.
*G21C 17/013*    (2006.01)
*G01B 17/02*    (2006.01)
(Continued)

(52) U.S. Cl.
CPC ........... *G21C 17/013* (2013.01); *G01B 17/02* (2013.01); *G01J 3/108* (2013.01); *G01N 33/28* (2013.01);
(Continued)

(58) Field of Classification Search
CPC . G21C 17/013; G21C 17/022; G01R 33/1215
See application file for complete search history.

(56) References Cited

U.S. PATENT DOCUMENTS 3,505,597 A * 4/1970 Cronin ................... G01R 31/12
                                                367/113
3,707,673 A * 12/1972 Carter .................... G01R 31/12
                                                324/532
(Continued)

FOREIGN PATENT DOCUMENTS

CN      1372645 A      10/2002
CN      1789955 A      6/2006
(Continued)

OTHER PUBLICATIONS

Translation of JP 2016148575 by Global Dossier (Year: 2016).*
(Continued)

*Primary Examiner* — Nicholas Kiswanto
*Assistant Examiner* — Christopher A Buksa
(74) *Attorney, Agent, or Firm* — Sage Patent Group

(57) ABSTRACT

An inspection system for inspecting a machine includes an inspection vehicle constructed for wireless operation while submersed in a dielectric liquid medium. The inspection vehicle is self-propelled. A controller is operative to direct the activities of the inspection vehicle. A plurality of status interrogation systems is disposed on the inspection vehicle. The status interrogation systems are operative to capture inspection data regarding a plurality of inspection procedures performed on the machine.

16 Claims, 11 Drawing Sheets

Related U.S. Application Data

(60) Provisional application No. 62/431,323, filed on Dec. 7, 2016.

(51) Int. Cl.
| | | |
|---|---|---|
| *G01J 3/10* | (2006.01) | |
| *G01N 1/10* | (2006.01) | |
| *G01N 33/28* | (2006.01) | |
| *G01R 33/12* | (2006.01) | |
| *G01S 15/46* | (2006.01) | |
| *G05D 1/00* | (2006.01) | |
| *G21C 17/01* | (2006.01) | |
| *H01F 27/12* | (2006.01) | |

(52) U.S. Cl.
CPC ......... *G01R 33/1215* (2013.01); *H01F 27/12* (2013.01); *G01N 2001/1031* (2013.01); *G01S 2015/465* (2013.01); *G05D 1/0038* (2013.01); *G21C 17/01* (2013.01)

(56) References Cited

U.S. PATENT DOCUMENTS

| | | | | |
|---|---|---|---|---|
| 3,731,752 | A * | 5/1973 | Schad | G01R 33/04 |
| | | | | 175/45 |
| 3,732,726 | A * | 5/1973 | Ferber | G01B 7/13 |
| | | | | 324/229 |
| 6,104,970 | A | 8/2000 | Schmidt et al. | |
| 7,615,007 | B2 * | 11/2009 | Shults | A61B 5/14865 |
| | | | | 600/347 |
| 2004/0123681 | A1 | 7/2004 | Thomas et al. | |
| 2006/0290779 | A1 | 12/2006 | Reverte et al. | |
| 2007/0125289 | A1 | 6/2007 | Asfar et al. | |
| 2015/0369751 | A1 | 12/2015 | Cheim et al. | |
| 2017/0054923 | A1 * | 2/2017 | Thompson | G01J 5/0096 |

FOREIGN PATENT DOCUMENTS

| | | | | |
|---|---|---|---|---|
| CN | 101551434 | A | 10/2009 | |
| CN | 201382868 | Y | 1/2010 | |
| CN | 102395872 | A | 3/2012 | |
| CN | 102520324 | A | 6/2012 | |
| CN | 104316362 | A | 1/2015 | |
| CN | 204359759 | U | 5/2015 | |
| CN | 204439417 | U | 7/2015 | |
| CN | 104931300 | A | 9/2015 | |
| CN | 105026112 | A | 11/2015 | |
| CN | 105182141 | A | 12/2015 | |
| JP | 63-47678 | | 2/1988 | |
| JP | 51-63694 | | 10/1995 | |
| JP | 11-326429 | | 11/1999 | |
| JP | 2012-220495 | | 11/2012 | |
| JP | 5872127 | | 3/2016 | |
| JP | 2016148575 | A * | 8/2016 | ............ G01B 11/16 |
| WO | WO 2014/120568 | A1 | 8/2014 | |

OTHER PUBLICATIONS

International Search Report and Written Opinion of the International Searching Authority, PCT/IB2017/001628, dated Jul. 5, 2018, 17 pages.
Christ, R., et al., "The ROV Manual," 1st Edition, Butterworth-Heinmann, Jul. 9, 2007, (For Exclusive Use by European Patent Office Sites Only, Copyright Elsevier B.V.) 318 pages.
International Preliminary Examination Report, PCT/IB2017/001628, dated Jun. 11, 2019, 11 pages.
First Office Action, Chinese Patent Application No. 201780086222.1, dated Nov. 2, 2022, 16 pages.
He Xin, "Ultrasonic Positioning System For Transformer Partial Discharge Based on Wireless Sensor Network," Chinese Master's Theses Full-text Database Engineering Science and Technology, Series II, Jul. 15, 2013; Section 1.3; 200921050415, China, 4 pages.
Wang Gang, "Development and Application of Comprehensive Processing System for Substation Monitoring Data Based on PCS-9700," Chinese Master's Theses Full-text Database Engineering Science and Technology, Series II , Jul. 15, 2015; Section 1.3.1; PCS-9700, China, 4 pages.
Office Action, Chinese Patent Application No. 2017800862221, dated May 12, 2023, 16 pages.
Office Action, Chinese Patent Application No. 201780086222.1, dated Jul. 28, 2023, 6 pages.

* cited by examiner

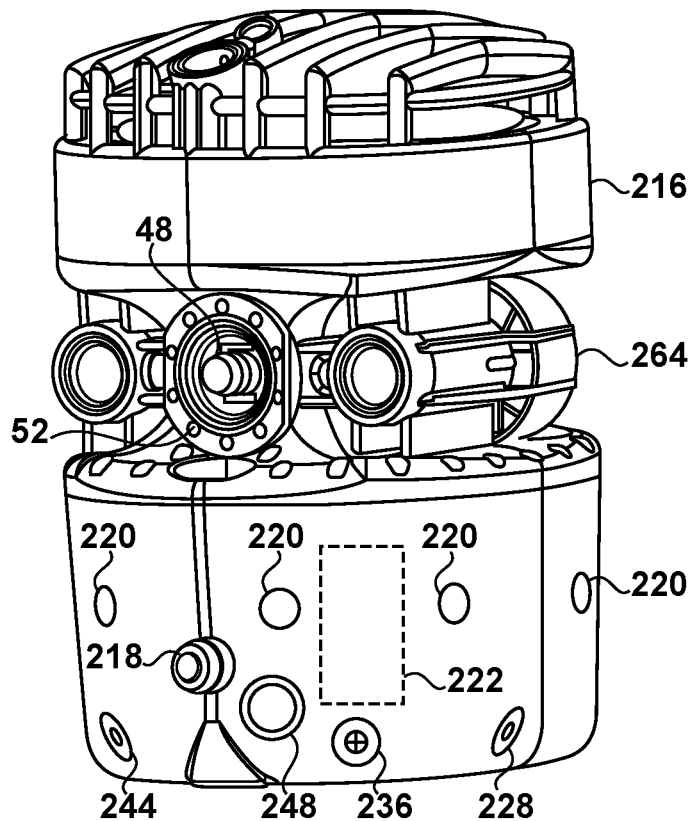
FIG.10
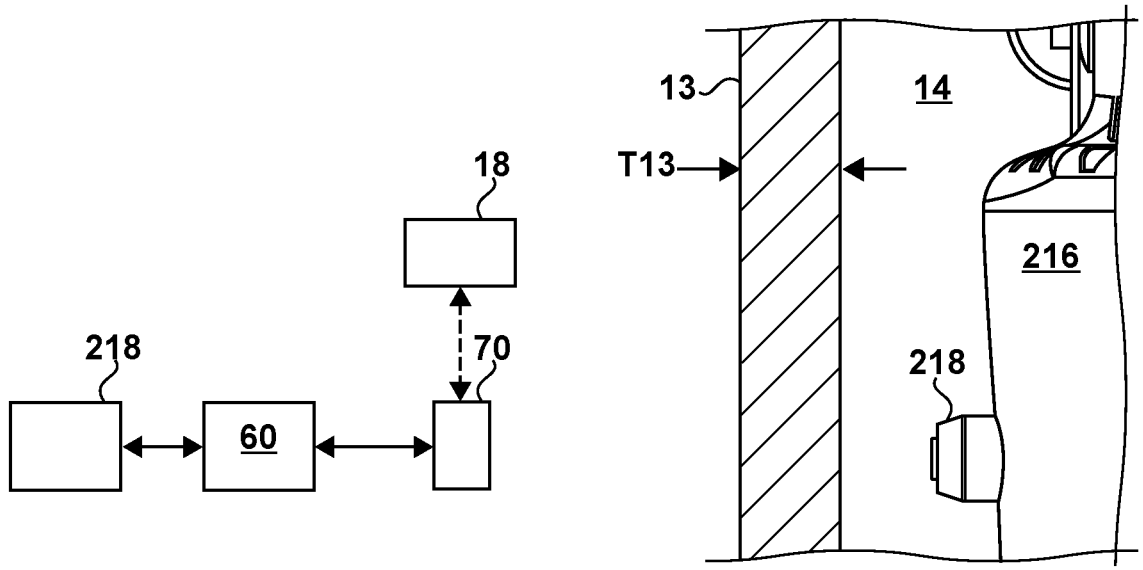
FIG.11
FIG.12

SYSTEMS AND METHODS FOR INSPECTING A MACHINE

TECHNICAL FIELD

The present application generally relates to inspection, and more particularly, but not exclusively, to systems and methods for inspecting machines.

BACKGROUND

Inspection systems for inspecting machines, e.g., transformers and other machines, remain an area of interest. Some existing systems have various shortcomings, drawbacks and disadvantages relative to certain applications. For example, some inspection systems require undesirable disassembly of the machine and/or undesirable draining of fluids, e.g., coolant oil, from the machine. Accordingly, there remains a need for further contributions in this area of technology.

SUMMARY

One embodiment of the present invention is a unique inspection system for inspecting a machine. Another embodiment is a unique method for performing an inspection of a machine. Other embodiments include apparatuses, systems, devices, hardware, methods, and combinations for machine inspection. Further embodiments, forms, features, aspects, benefits, and advantages of the present application shall become apparent from the description and figures provided herewith.

BRIEF DESCRIPTION OF THE FIGURES

The description herein makes reference to the accompanying drawings wherein like reference numerals refer to like parts throughout the several views, and wherein:

FIG. 10 illustrates some aspects of a non-limiting example of an inspection vehicle in accordance with an embodiment of the present invention.

FIG. 11 schematically illustrates some aspects of a non-limiting example of a status interrogation system in the form of an ultrasound sensor communicatively coupled to a controller, and to a base station computer via a wireless connection, in accordance with an embodiment of the present invention.

FIG. 12 illustrates some aspects of a non-limiting example of an inspection vehicle and a tank or housing wall having a wall thickness to be measured by an ultrasound sensor in accordance with an embodiment of the present invention.

DETAILED DESCRIPTION OF THE ILLUSTRATIVE EMBODIMENTS

Figure 1:
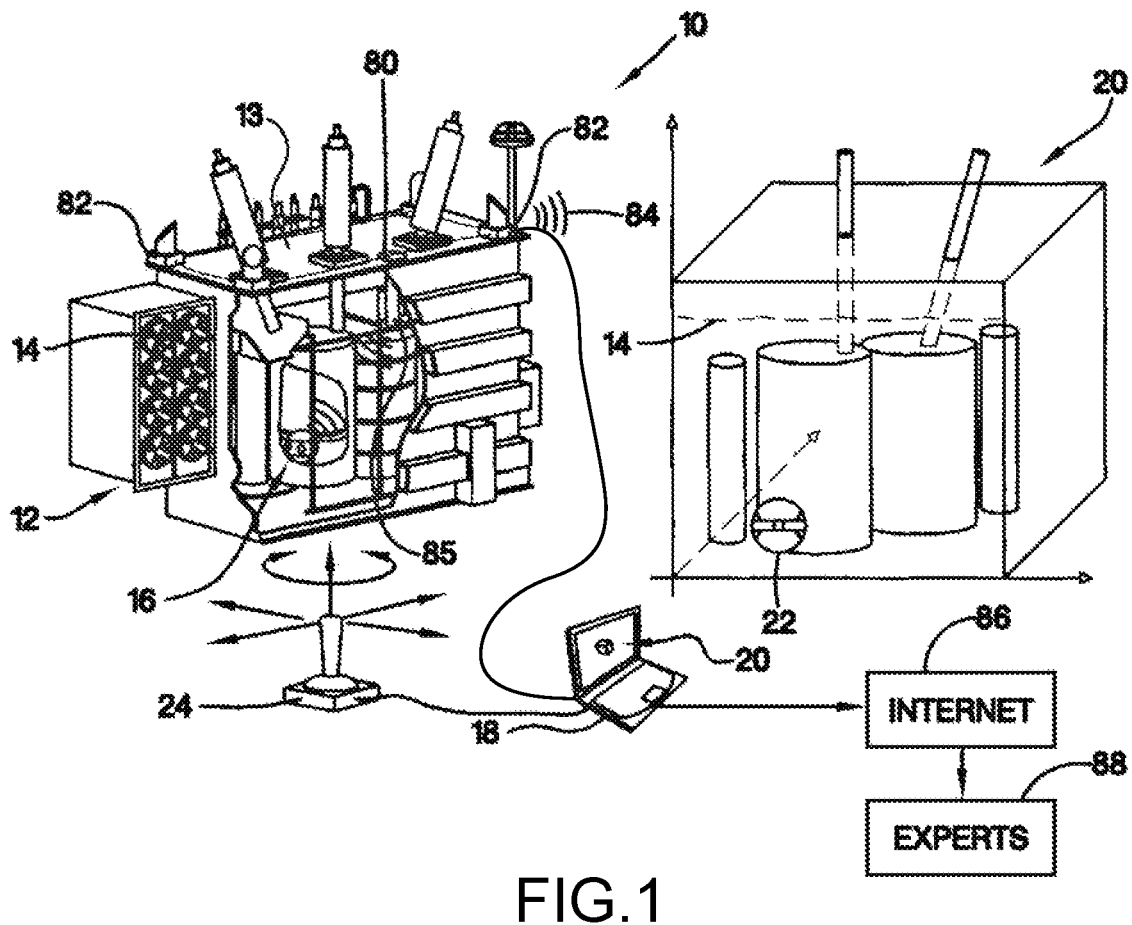
FIG. 1 is a schematic diagram of a system for in-situ inspection according to one exemplary embodiment of the present disclosure.
Figure 2:
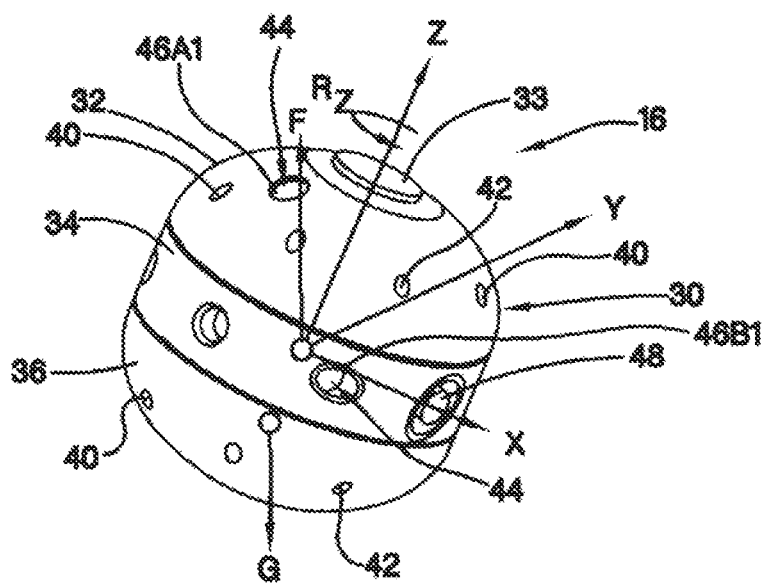
FIG. 2 is a perspective view of an inspection vehicle used within the system according to one exemplary embodiment of the present disclosure.
Figure 3:
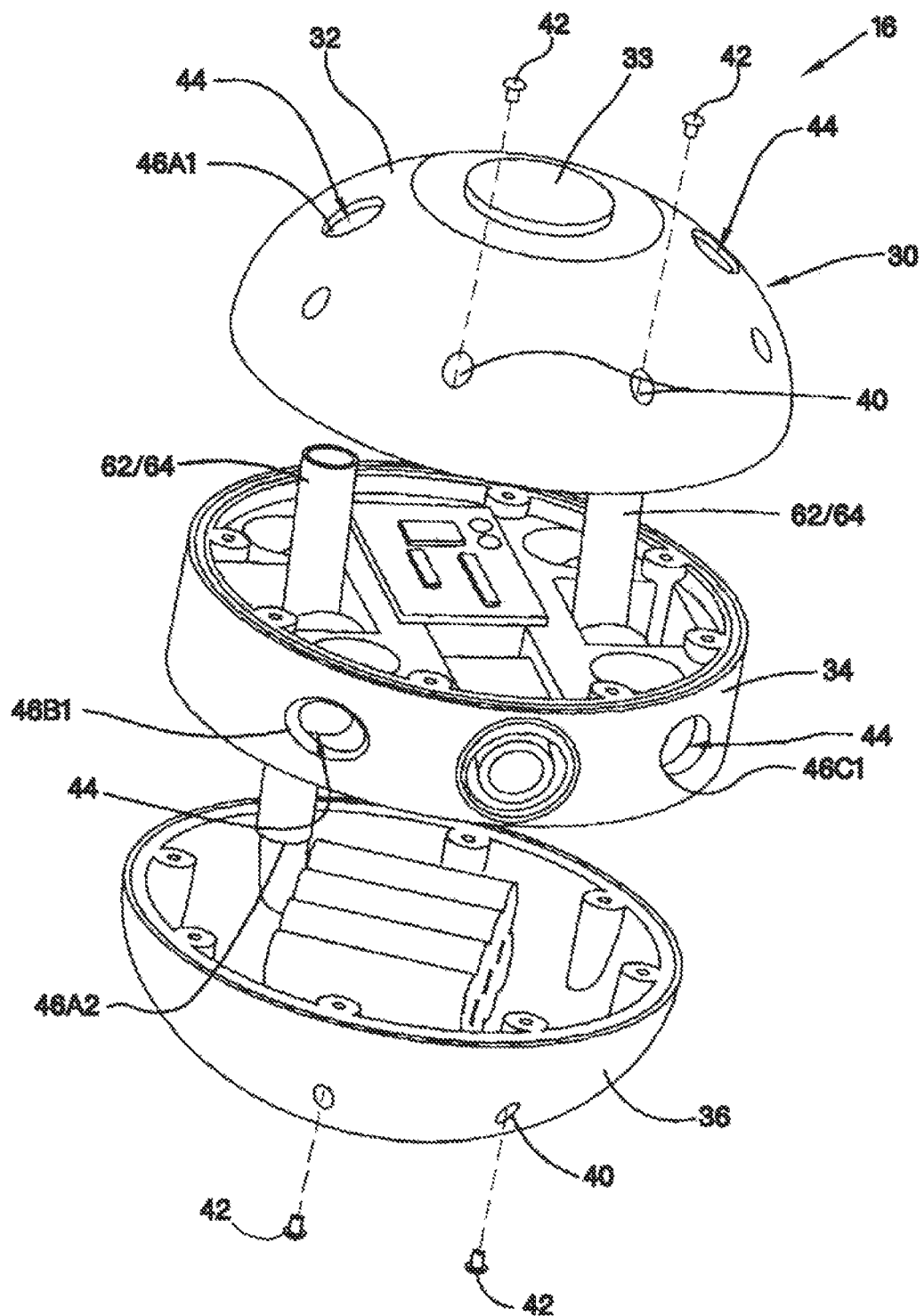
FIG. 3 is an exploded view of the inspection vehicle used within the system according to one exemplary embodiment of the present disclosure.
Figure 4:
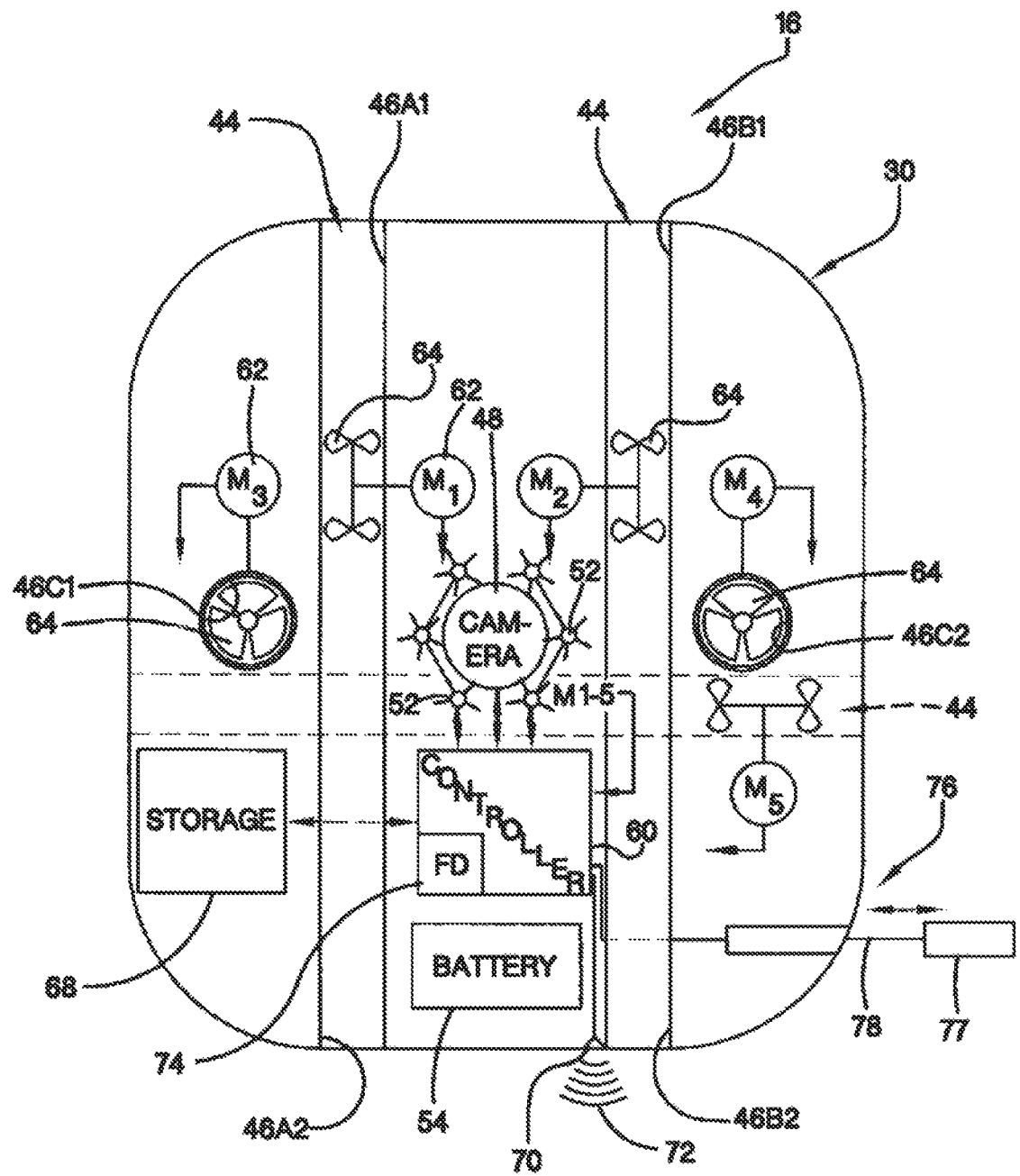
FIG. 4 is a schematic diagram of the inspection vehicle according to one exemplary embodiment of the present disclosure.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Referring to FIG. 1, a system for in-situ inspection of a liquid filled transformer designated generally by the numeral 10 is illustrated. It should be understood that while liquid filled electrical transformers are described and referenced in this application, the systems and methods described herein are not limited to liquid filled transformers, but on the contrary can be used with any liquid filled housing, structure or container wherein physical inspection, data collection, data transmittal and repair procedures or the like are desired without prior draining of the liquid from the housing. By way of example, and not limitation, in-situ inspection may be performed on/in potions of ship hulls, electrical interrupters, high voltage switch gears, nuclear reactors, fuel tanks, food processing equipment, floating roof storage system, chemical storage tank—or other apparatus of similar nature.

In one exemplary embodiment, the system 10 can be used for inspection, data transmittal and/or maintenance of a transformer 12. The transformer 12 contains high-voltage electrical components immersed in a dielectric cooling liquid 14 such as oil. Skilled artisans will appreciate that the inspection typically, but not necessarily, occurs when the transformer is offline or not in use. The transformer 12 utilizes the cooling liquid 14 to maintain temperature and disburse heat generated by the internal components during operation of the transformer 12. In some embodiments, the cooling liquid 14 may have dielectric properties such that electrical conduction is reduced or entirely eliminated in the fluid. The transformer 12 can be maintained in a sealed configuration so as to prevent contaminants or other foreign matter from entering therein. As used herein, a "sealed configuration" of the tank or housing 13 allows for conduit ducts or other hardware associated with the transformer 12 to extend through a wall via a sealed joint formed with the housing 13 to allow for connection to electrical components and/or monitoring devices maintained in the housing 13. The housing 13 includes at least one opening to allow for ingress into and egress out of the housing 13. An inspection vehicle 16, sometimes referred to as a "robot," is insertable into the housing 13 of the transformer 12 and is controlled either by un-tethered wireless remote control or through a tether connection.

A computational device 18, such as a laptop computer or other appropriate computing device can communicate with the inspection vehicle 16 either by direct connection through a tether or wirelessly. The computer 18 may maintain a virtual transformer image 20 of the internal construction of the transformer 12. In some embodiments, this virtual image can be a computer-aided-design (CAD) image generated in construction or design of the transformer. However, in other forms, images such as photographs or actual real time video generated by sensors and cameras associated with the inspection vehicle 16 may be utilized. As will be described in further detail, the computer 18 may utilize the virtual transformer image 20 in conjunction with a virtual inspection vehicle 22, to represent the actual inspection vehicle 16, so as to monitor the positioning of the inspection vehicle 16 within the transformer 12. A motion control input device, such as a joystick 24 can be connected to the computer 18 and/or directly to the inspection vehicle 16 to allow an operator to control movement of the inspection vehicle 16 inside the transformer 12. Control of the inspection vehicle 16 can be aided by observations of the virtual inspection vehicle 22 as it moves about the virtual transformer image 20. In other words, an operator can control movement of the inspection vehicle 16 based on the observed position of the inspection vehicle 16 within the transformer 12. Other types of motion control input devices, such as those used with video games, handheld computer tablets, computer touch screens or the like may be employed without deviating from the teachings herein. It should be understood that in some applications the operator may be located on site or near the apparatus to be inspected. However, in other applications the operator may be located off-site and indeed anywhere in the world and may communicate via an Internet or other network connection.

Referring now to FIGS. 2-5, the inspection vehicle 16 includes a vehicle housing 30 that is substantially cylindrical or spherical in construction with no significant protrusions or extensions that might otherwise be entangled with the internal components within the transformer 12. The vehicle housing 30 of the inspection vehicle 16 includes an upper cover 32 having a minimally extending nub 33, a middle section 34 and a lower cover 36. The nub 33 is sized so as to allow for grasping of the inspection vehicle 16 from within the transformer 12 by a tool or by an operator's hand. The nub 33 could have other shapes, such as a loop, to facilitate easy grasping, depending on the type of tool used to grasp the inspection vehicle 16. The cover 32, the middle section 34 and the cover 36 can be secured to one another with fastener apertures 40 that extend through at least the covers 32 and 36 so as to receive fasteners 42 to allow for attachment to the middle section 34. In most embodiments the fasteners 42 are maintained flush with the surface of the cover so as to minimize drag and prevent entanglement with internal components of the transformer 12. Other forms of mechanical fastening may be used, such as threaded engagement, press-fit, or mechanical clip or the like. Further, in some embodiments, the inspection vehicle 16 may only include two sections and in other embodiments the inspection vehicle 16 may include four or more sections.

Extending through the vehicle housing 30 are at least two pump flow channels designated generally by the numeral 44. These extend vertically and horizontally through the vehicle housing 30 and are configured so as to be sealed from the internal components of the vehicle housing 30. Each flow channel 44 provides a pair of ports 46. As shown in the drawings, numeric and alphabetic designations are provided so as to identify particular ports. For example, port 46A1 is at one end or side of the vehicle housing 30 while the opposite end of the flow channel 44 is designated by port 46A2. As such, the fluid maintained within the transformer can flow from one port 46A1 through and exit out port 46A2. In a similar manner, the oil may flow through port 46B1 and out through port 46B2. As will be discussed, components maintained within the channels move the fluid in either direction, through the inspection vehicle 16 and thus allow the inspection vehicle 16 to move within the transformer 12. It should be appreciated that alternate flow channel configurations could be implemented. For example, fluid could enter the inspection vehicle 16 through a single inlet and internal valves could route the fluid to all outlet ports. In another example, the vertical path could have one inlet port and two or more outlet ports. At least one sensor 48 is carried by the vehicle housing 30 and in some embodiments the sensor 48 is a camera. Other sensors can be used in some embodiments such as, by way of non-limiting examples, proximity sensors, acoustic sensors, electromagnetic sensors, voltage sensors, amperage sensors, pressure sensors and temperature sensors. The camera 48 is configured to receive and transmit images through a plurality of wavelength images of the internal components of the transformer 12. The wavelengths can include visible, infrared, or others as desired. These images allow an operator to monitor and inspect various components within the transformer 12.

In some embodiments, the vehicle housing 30 can include one or more light sources 52 which facilitate illumination of the area surrounding the inspection vehicle 16. In some embodiments the lights 52 can be light emitting diodes, but it will be appreciated that other illumination devices can be used. For example, one or more of the lights 52 can include ultraviolet (UV) frequencies that may be used to cure UV hardened adhesives or the like. The illumination devices are oriented so as to illuminate the viewing area of the camera 48. In some embodiments, the operator can control the intensity and wavelength of the light.

A battery pack 54 is maintained within the inspection vehicle 16 so as to power the internal components such as the sensor 48, the lights 52 and a controller 60. The controller 60 operates the sensor 48 and lights 52 and also controls operation of a motor 62 and a pump 64 which are used in combination with each of the provided pump flow channels 44. The controller 60 maintains the necessary hardware and software to control operation of the connected components and maintain the ability to communicate with the computer 18 as well as with other devices. The controller 60 provides functionality in addition to controlling the motion of the inspection vehicle 16. For example, the controller 60 can provide for a data recording function so that a high-resolution, high speed video of the entire inspection area generated by the sensor 48 can be recorded and stored onboard by the storage device 68. On board storage may be used in instances where wireless streaming of the video is interrupted or the antenna transmission of the wireless signals has a lower than desired bandwidth. Skilled artisans will appreciate that the sensor 48 may also be a thermal camera, a sonar sensor, a radar sensor, a three-dimensional vision sensor, or any combination of sensors.

Each motor 62 is reversible so as to control the flow of fluid through the flow channels by the pump 64. In other words, each motor is operated independently of one another so as to control operation of the associated thruster pump 64 such that rotation of the pump 64 in one direction causes the fluid to flow through the flow channel 44 in a specified direction and thus assist in propelling the vehicle housing 30 in a desired direction. The pump 64, which may also be referred to as a thruster pump, is shown as being a propeller type configuration, but other configurations such as a paddle-type pump or gear pump could be utilized.

In some embodiments, a single motor may be used to generate a flow of fluid through more than one channel. In other words, the vehicle housing 30 could provide a single inlet and two or more outlets. Valves maintained within the vehicle housing 30 could be used to control and re-direct the internal flow of the fluid and, as a result, control movement of the vehicle housing 30 within the transformer tank or housing 13. By coordinating operation of the motors with the controller, and thus the oil flowing through the vehicle housing 30, the inspection vehicle 16 can traverse all areas of having sufficient space within the transformer 12. Moreover, the inspection vehicle 16 is able to maintain an orientational stability while maneuvering in the transformer tank or housing 13. In other words, the inspection vehicle 16 is stable such that it will not move end-over-end while moving within the transformer tank or housing 13. The vehicle housing 30 of the inspection vehicle 16 provides for a center of gravity designated by the capital letter G. The inspection vehicle 16 components are designed so that the center of gravity G is lower than the center of the buoyant force of the inspection vehicle 16 designated by the capital letter F. As skilled artisans will appreciate, this enables the inspection vehicle 16 to be provided with stability during traversal motion.

The vehicle housing 30 also carries a data storage device 68 which collects the data from the sensor 48 and is adequately sized to provide for storage of video or still images taken by a camera. The storage device 68 is connected to the controller 60 so as to provide for reliable transfer of the data from the sensor/camera 48 to the storage device 68. It will be appreciated that in some embodiments the storage device 68 is connected directly to the sensor 48 and the controller receives the data directly from the storage device 68. An antenna 70 is connected to the controller 60 for the purpose of transmitting data collected from the sensor 48 and also for sending and receiving control signals for controlling the motion and/or direction of the inspection vehicle 16 within the transformer 12. The antenna generates a wireless signal 72 that can be detected by the computer 18 or any intermediate device. A failure detection module 74 (designated as FD in FIG. 4) may be included in the controller so as to shut down the internal components within the inspection vehicle 16 if a system failure is detected. For example, if a low battery level is detected by the controller 60, the module 74 and the controller 60 can begin a controlled shutdown of the inspection vehicle 16 which would cause the inspection vehicle 16 to float to the surface due to its positive buoyancy. In another example, a loss of connection to the remote system could also trigger a shutdown.

After floating to the surface, the vehicle housing 30 can be grasped by the nub 33. A borescope 76 may also be carried by the vehicle housing 30. One end of the borescope provides a camera 77 or other sensor connected to a retractable fiber-optic cable 78 which is connected at its opposite end to the controller 60. When in a retracted position the camera 77 is flush with the surface of the vehicle housing 30 so as to prevent entanglement with the components inside the transformer 12. When inspection of hard to view items is needed, such as the windings of the transformer 12, the cable 78 is extended while the inspection vehicle 16 is maintained in a stationary position. After images and other data are collected by the camera 77, the cable is retracted. As a result, the borescope 76 allows further detailed inspection of the transformer 12.

As noted previously, the inspection vehicle 16 is configured so as to easily move around the obstacles within the transformer 12. The vehicle housing 30 is a cylindrical-shaped with sphere ends or sphere shaped configuration and is provided with a buoyant design so as to allow the inspection vehicle 16 to float to the top of the oil when it is powered off purposefully or accidentally. The inspection vehicle 16 is configured so as to allow for the thruster pumps 64 to move the inspection vehicle 16 around by selective actuation of each pump. As a result, the inspection vehicle 16 has four degrees of freedom or motion: X, Y, Z and rotation around Z. As a result, by controlling the direction of the pump thrusters 64, the inspection vehicle 16 can be easily moved.

Referring back to FIG. 1, it can be seen that the transformer 12 has at least one transformer hole 80. In general operation, the oil is inserted through any number of holes located in the top of the tank. Holes 80 may also be provided at the bottom of the tank to allow for the fluid to be drained. The holes 80 are provided with the appropriate plugs or caps. Accordingly, it will be appreciated that the size of the inspection vehicle 16 must be such that it can fit within the hole 80.

The transformer 12 may be configured with a plurality of transmit signal receivers 82 mounted on the upper corners, edges or other areas of the transformer 12, or in nearby proximity to the transformer 12. The transmit signal receivers 82 receive the wireless signal 72 from the inspection vehicle 16 to determine the position of the inspection vehicle 16 in the transformer tank or housing 13. The receivers 82 use triangulation, based on the signals 72 received or other methodology, to determine a position of the inspection vehicle 16 in the transformer tank or housing 13. This position information is then transmitted by a signal 84, either wired or wirelessly, to the computer 18. Additionally, the information collected by the sensor 48, such as the visual data, is transferred to the computer or other visual receiving device separately. In other words, the informational data generated by the sensor 48 is transmitted to the computer 18 through the fluid and the tank wall with the openings 80. Use of these different communication paths may be used to prevent interference between the signals; however, some embodiments may utilize the same communication path to transfer data related to positioning, data information, and control information as appropriate. Reliable communication for the motion control of the inspection vehicle 16 and data/video streaming are required for the transformer 12 In-situ inspection. Because of the dielectric aspect of the transformer coolant oil, the inspection vehicle 16 can be controlled by radio frequencies rather effectively. The video streaming for a Wi-Fi camera (e.g. 4.2 GHz) has been proven to be sufficient. To ensure reliable communication between the inspection vehicle 16 and the computer 18, a transceiver 85 may be inserted into the cooling oil tank through the service opening on the top of the transformer 12.

In most embodiments, the transceiver 85 is used to exchange data information from the sensor 48 and the camera 77, via the controller 60 to the computer 18; and motion control or maneuvering signals from the joystick 24 via the computer 18 to the controller 60 so as to operate the motors 62 and thrusters 64. The signal 84, transmitted by the receiver 82 is used by the computer 18 to provide a separate confirmation of the position of the inspection vehicle 16 within the transformer tank or housing 13.

Wireless signals transmitted between inspection vehicle 16 and computer 18, and the respective transmitters, receivers and transceivers for the various purposes described herein can occur in a variety of manners, including electronic wireless signals of various frequencies, powers, and protocols. In some applications the communication between the inspection vehicle 16 and the base station (computer 18) can be supplemented with a repeater or relay station, but not all embodiments need include such devices. The manners of transmission between devices need not be identical in all embodiments. To set forth just a few examples, the transmitter and/or receiver used for broadcast of signals from the base station (computer 18) can transmit in power that ranges from 1 W to 5 W. Other power output levels may be employed in other embodiments. The base station transmitter can also transmit in frequencies that that range from about 300 MHz to about 5 GHz, and in some forms are at any of 300 MHz, 400 MHz, 433 MHz, 2.4 GHz, and 5 GHz. Other frequencies may be employed in other embodiments. Transmission can occur using any variety of protocols/formats/modulation/etc. In one example, transmission from the base station can use digital radio communications such as that used for RC model cars/boats/airplanes/helicopters. The transmission can also occur as TCP/IP or UDP, it can occur over WiFi radios, serial communication over Bluetooth radios, etc. In one particular form, video transmissions can occur as streaming for a Wi-Fi camera over 2.4 GHz.

In much the same manner as the transmitter and/or receiver of the base station (computer 18), the transmitter and/or receiver of the inspection vehicle can transmit in power that ranges from 250 mW to 3 W. Other power output levels may be employed in other embodiments. The inspection vehicle can also transmit in frequencies that that range from about 300 MHz to about 5 GHz, and in some forms are at any of 300 MHz, 400 MHz, 433 MHz, 2.4 GHz, and 5 GHz. Other frequencies may be employed in other embodiments. Transmission can occur using any variety of protocols/formats/modulation/etc. In one example, transmission from the inspection vehicle can use digital radio communications such as that used for RC model cars/boats/airplanes/helicopters. The transmission could be video over IP, and one embodiment of IP could be Wi-Fi/WLAN. In one non-limiting embodiment the transmission can therefore occur as TCP/IP or UDP, it can occur over WiFi radios, serial communication over Bluetooth radios, etc. In one particular form, video transmissions can occur as streaming for a Wi-Fi camera over 4.2 GHz. In short, a variety of transmission techniques/approaches/protocols/frequencies/etc are contemplated herein.

The computer 18 receives the position signals 84 and information signals 72 and in conjunction with the virtual image 20 correlates the received signals to the virtual image so as to allow an operator to monitor and control movement of the inspection vehicle 16. This allows the operator to inspect the internal components of the transformer 12 and pay particular attention to certain areas within the transformer 12 if needed. By utilizing a virtual image of the internal features of the transformer 12 and the position of the inspection vehicle 16 with respect to those virtual features, the image obtained can be matched with the corresponding site inside the actual transformer tank or housing 13. Based on the visual representation of the transformer image 20 and the virtual inspection vehicle 22 in relation to the image, an operator can manipulate the joystick 24 response. The computer 18 receives the movement signals from the joystick 24 and transmits those wirelessly to the antenna 72, whereupon the controller 60 implements internally maintained subroutines to control the pump thrusters 64 to generate the desired movement. This movement is monitored in real-time by the operator who can re-adjust the position of the inspection vehicle 16 as appropriate.

In some embodiments the computer 18 can be connected to a network 86, such as the Internet, so as to allow for the images or sensor data to be transferred to experts, who may be remotely located, designated by the block 88 so that their input can be provided to the operator so as to determine the nature and extent of the condition within the transformer 12 and then provide corrective action as needed. In some embodiments, control of the inspection vehicle 16 can also be transferred to an expert, who may be remotely located. In such embodiments, the expert would have another computer that can send control signals via a network to the local computer 18 that in turn sends signals to control the inspection vehicle 16 as described above.

Figure 5:
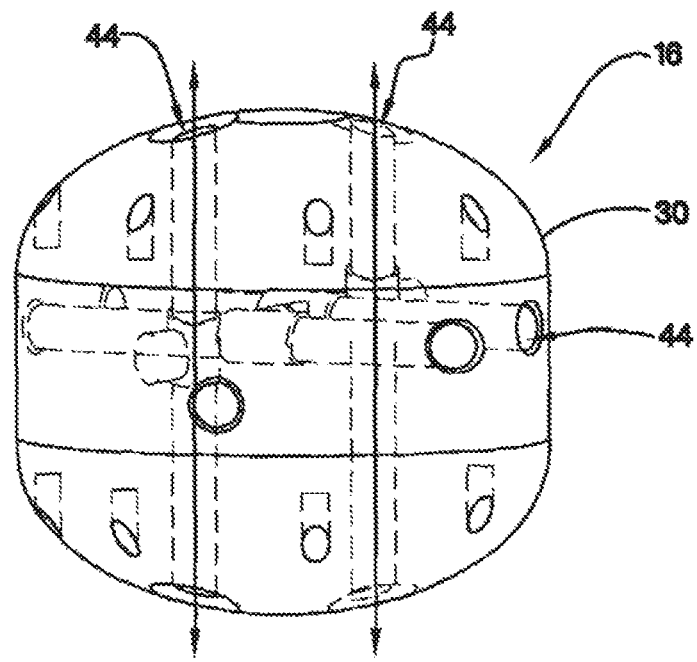
FIG. 5 is a schematic diagram of the inspection vehicle according to one exemplary embodiment of the present disclosure where two pumps under one control move the device in the Z direction.

Referring now to FIGS. 5-9, it can be seen that control of the motors and pump thrusters and their direction of fluid flow through the channels can control the motion of the inspection vehicle 16 within a liquid. For example, FIG. 5 shows the utilization of two pumps under one control so as to move the inspection vehicle 16 in a Z direction. To drive along the Z axis and to remain a stable depth, the Z axis thrusters have to run continuously. The Z thruster action can be controlled either manually by the operator or automatically by the controller. As used herein, the terminology "one control" refers to operating two pumps to operate in conjunction with one another so that the fluid flow is uniformly in one direction or the other.

Figure 6:
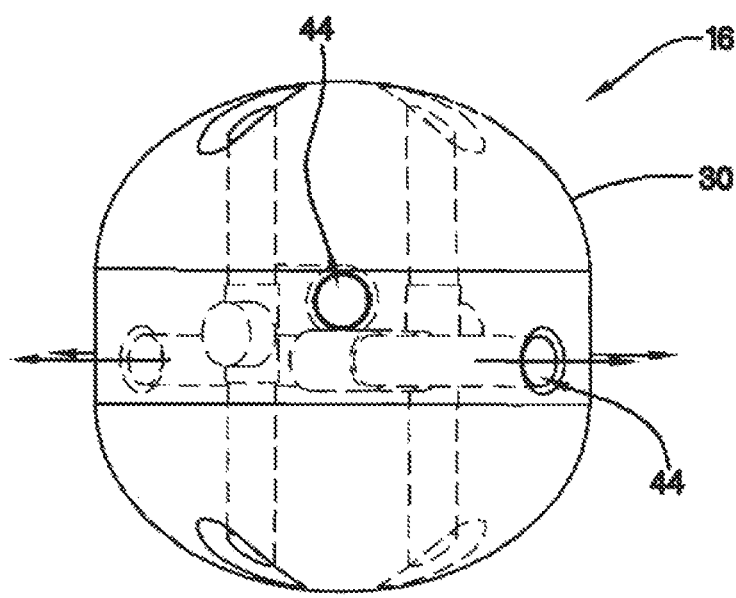
FIG. 6 is a schematic diagram of the inspection vehicle according to one exemplary embodiment of the present disclosure where two pumps under two controls move the device in the X direction.
Figure 7:
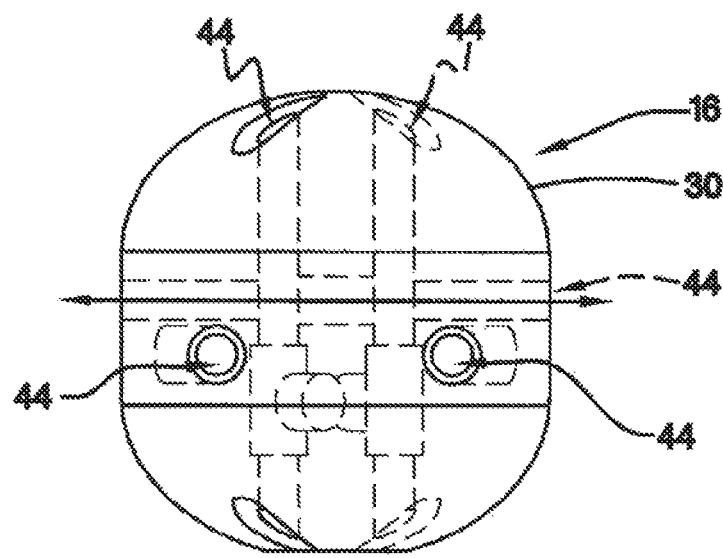
FIG. 7 is a schematic diagram of the inspection vehicle according to one exemplary embodiment of the present disclosure where a single pump under one control moves the device in the Y direction.

In FIG. 6 it can be seen that an X direction can be obtained by utilizing two pumps under two controls so as to allow for movement in an X direction. As used herein, operation of "two pumps under two controls" means that the controller operates the pumps separately from one another. In FIG. 7 it can be seen that the inspection vehicle 16 is movable along the Y direction wherein one pump is utilized under one control. It will be appreciated that FIG. 7 is a side view of FIG. 6 and at a slightly different elevation with respect to the X directional flow channels. As mentioned above, other embodiments could use different combinations of channels. For example, the three or four channels could exist in the Z direction. Also, other embodiments could have one inlet port and two outlet ports for a channel, or vice versa, or even use a different number of inlets and outlets. The number of pumps could also vary. For example, one pump could be used to control the flow of fluid from one inlet port which is then output through four outlet ports.

Figures 8A, 8B:
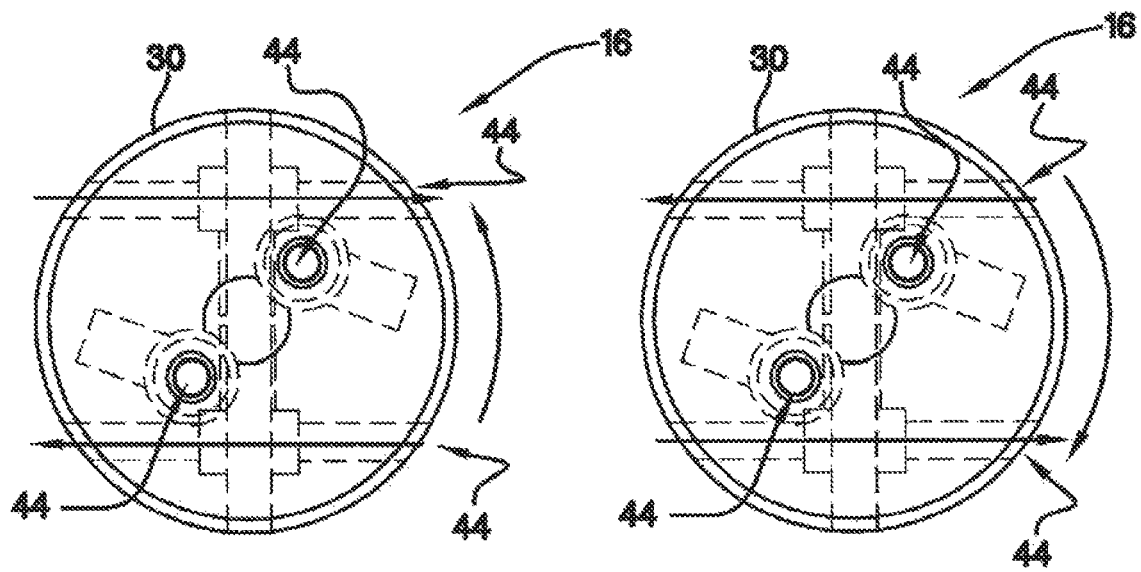
FIGS. 8A and 8B are schematic diagrams of the inspection vehicle according to one exemplary embodiment of the present disclosure wherein two pumps under one control operate to rotate the device in a counter-clockwise direction and in a clockwise direction, respectively.
Figure 9A:
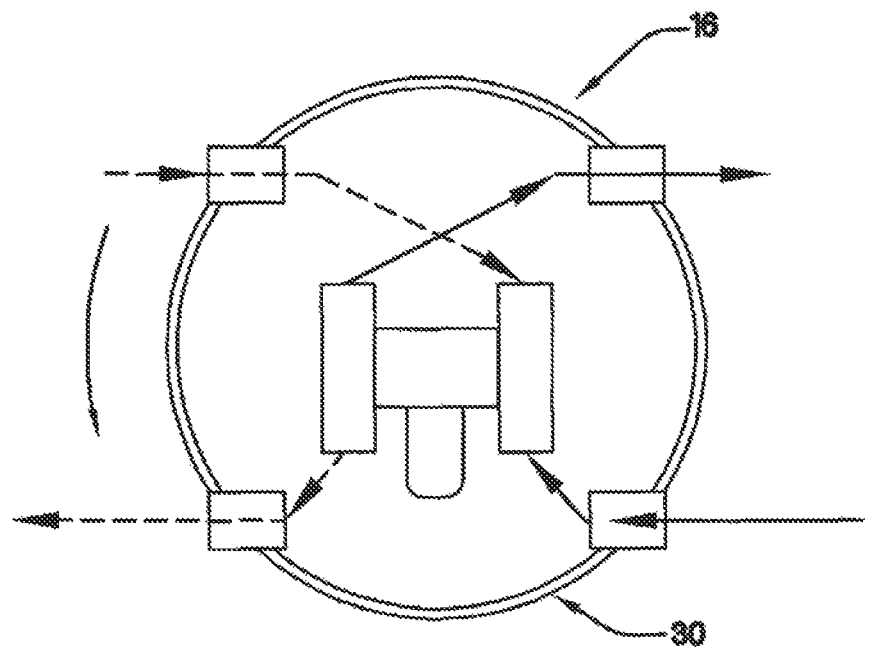
FIGS. 9A and 9B are schematic diagrams of the inspection vehicle according to one exemplary embodiment of the present disclosure wherein one pump operates to rotate the vehicle in a counter-clockwise direction and in a clockwise direction, respectively.
Figure 9B:
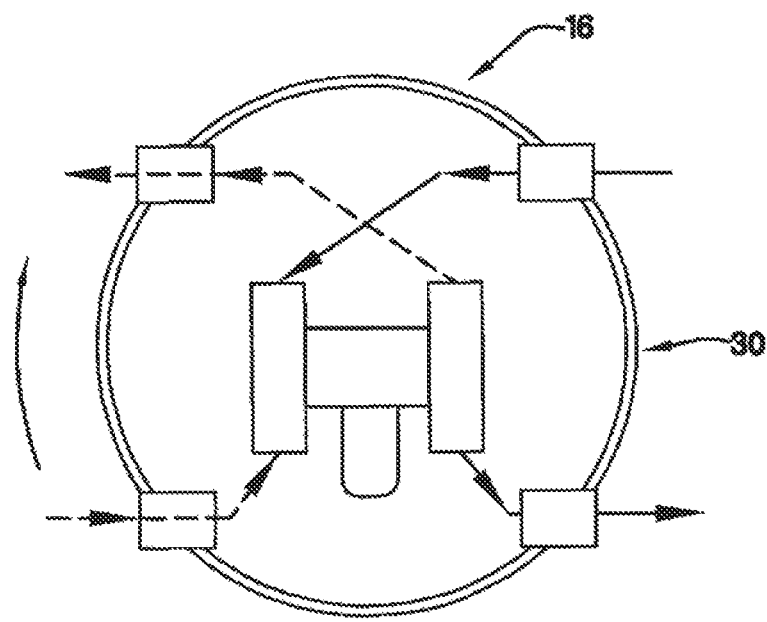

In FIGS. 8A and 8B it can be seen that two pumps under one control allow for rotation of the inspection vehicle 16. In FIG. 8A, by directing the fluid flow in one direction through one channel and an opposite direction in another channel, counter-clockwise rotation can be obtained. By reversing the flows in both channels, clockwise rotation can be obtained as seen in FIG. 8B. In another variation, FIGS. 9A and 9B show rotation of the inspection vehicle 16 utilizing one pump under one control wherein the flow is directed from one side of the inspection vehicle 16 into the inspection vehicle 16 and then back out the same side. A corresponding flow is provided by the opposite side of the inspection vehicle 16 so as to provide for rotation about the Z axis. Reversing the flow provides a corresponding reversal of the rotation of the inspection vehicle 16 along the Z axis.

The inspection vehicle 16 allows for visual and other inspection without draining transformer oil. This is accomplished by being able to drive the inspection vehicle 16 in the oil and perform visual or other inspection through the oil. The inspection vehicle 16 is constructed to be resistant to an oil environment and is properly sealed. Additionally, the inspection vehicle 16 is small enough to be put inside a transformer tank or housing 13 using existing service holes, e.g. those used for filling the transformer oil. As a result, it is not needed to unseal the transformer tank top completely. Another aspect is that the inspection vehicle 16 can be controlled from the outside of the transformer using a joystick 24 and computing device 18 which may also be used for presenting visual data from the sensor(s).

As internal regions of a transformer have no ambient light, the sensor 48 utilizes a supporting light source carried by the inspection vehicle 16. Various wavelengths of light may be used (visible and/or non-visible light) for detailed inspection of the transformer 12 components inside. A remotely controlled arm that guides a thin fiber-optic camera head inside the transformer 12 winding block may also be used. Still another aspect of the inspection vehicle 16 is that all materials employed in the construction of the inspection vehicle 16 are oil compatible. This is to avoid any type of contamination introduced by the inspection vehicle 16, so that the transformer 12 can directly return to operation after the inspection of inspection vehicle 16 without oil treatment.

Referring to FIG. 10, some aspects of a non-limiting example of an inspection vehicle 216 in accordance with an embodiment of the present invention are illustrated. Inspection vehicle 216 may be used in conjunction with in-situ inspection system 10 in addition to or in place of inspection vehicle 16. Inspection vehicle 216 includes a status interrogation system in the form of an ultrasound sensor 218. A status interrogation system is a system operative to capture data for contemporaneously or subsequently determining the status of a component, feature, system, subsystem or other aspect of the machine being inspected, e.g., of transformer 12, tank or housing 13, cooling liquid 14 and/or related components or features. Inspection vehicle 216 also includes many or most features described above with respect to inspection vehicle 16 in order to perform inspections, and performs most or all of the same functions as described above with respect to inspection vehicle 16. For example, the features include but not limited to sensor 48, e.g., a camera; light sources 52; battery pack 54; controller 60; storage device 68; antenna 70 and other components and features for transmitting and receiving wireless signals, e.g., signals 72 and other wireless signals, to and from computer 18 through dielectric coolant liquid 14, and other components and features for wirelessly self-propelling around transformer 12, and performing inspection, data transmittal and/or maintenance of transformer 12 immersed in dielectric cooling liquid inside tank or housing 13. Computer 18 serves as a base station for wirelessly transmitting data, e.g., commands, to the inspection vehicle, e.g., for directing the actions of the inspection vehicle while immersed within dielectric cooling liquid 14, including propulsion and inspection activities; and for wirelessly receiving data transmitted from the inspection vehicle, e.g., position data, and sensor and status interrogation system data. Although the present embodiment is wireless, it will be understood that other embodiments may employ wired connections in addition to or in place of some or all wireless connections. In place of pumps 64, inspection vehicle 216 employs shrouded propellers 264, which provide, at least in part, propulsion for inspection vehicle 216 while immersed within cooling liquid 14.

Referring to FIG. 11, ultrasound sensor 218 is communicatively coupled to controller 60, and wirelessly to computer 18 via controller 60, e.g., and antenna 70. Ultrasound sensor 218 is operative to generate and detect ultrasound pulses, e.g., through a couplant, such as dielectric cooling liquid 14 in transformer tank or housing 13, and to record the echo time of each transmitted ultrasound pulse to determine wall thickness of structures associated with transformer 12 and/or tank or housing 13, e.g., when directed by controller 60, for example, in response to commands received from computer 18 via antenna 70. In addition to determining metallic wall thickness, ultrasound sensor 218 is also operative to determine thicknesses of other materials and structures, including paint or other protective coating thickness, insulation thickness for one or more insulated structures or devices, and the thickness of any sediment build-up, e.g., at the bottom of tank or housing 13. In some embodiments, ultrasound sensor 218 is a smart sensor operative to determine thickness based on echo time, and to transmit the thickness data to controller 60. In other embodiments, controller 60 and/or computer 18 may be operative to determine the wall thickness of structures, features and sediment based on echo return time, e.g., based on the time between the sending of each ultrasound pulse and the receipt of the ultrasound pulse as reported by ultrasound sensor 218. In the illustration of FIG. 12, in order to measure the local thickness T13 of the tank or housing 13 wall, inspection vehicle 216 propels itself toward the wall until ultrasound sensor 218 is touching the wall, after which time it emits the ultrasound pulses, detects the echoes and determines pulse return time to determine thickness. Likewise when measuring the thickness of other structures or features: inspection vehicle 216 propels itself toward the feature until ultrasound sensor 218 is touching the feature, at which time the interrogative pulses are sent and their echoes subsequently received in order to determine thickness based on the echo time. In some embodiments, ultrasound sensor 218 and/or controller 60 and/or computer 18 may include and employ or access lookup tables, equations or other reference materials in order to determine thickness based on echo return time. The raw sensor data and/or thickness data may be wirelessly transmitted from inspection vehicle 216 to computer 18 via antenna 70. Camera 48 and light sources 52 may be employed to further investigate regions found using ultrasound sensor 218 to have an undesirable thickness, e.g., a reduced insulation thickness, a reduced wall thickness or an undesirable concentration of sediment.

Figure 13:
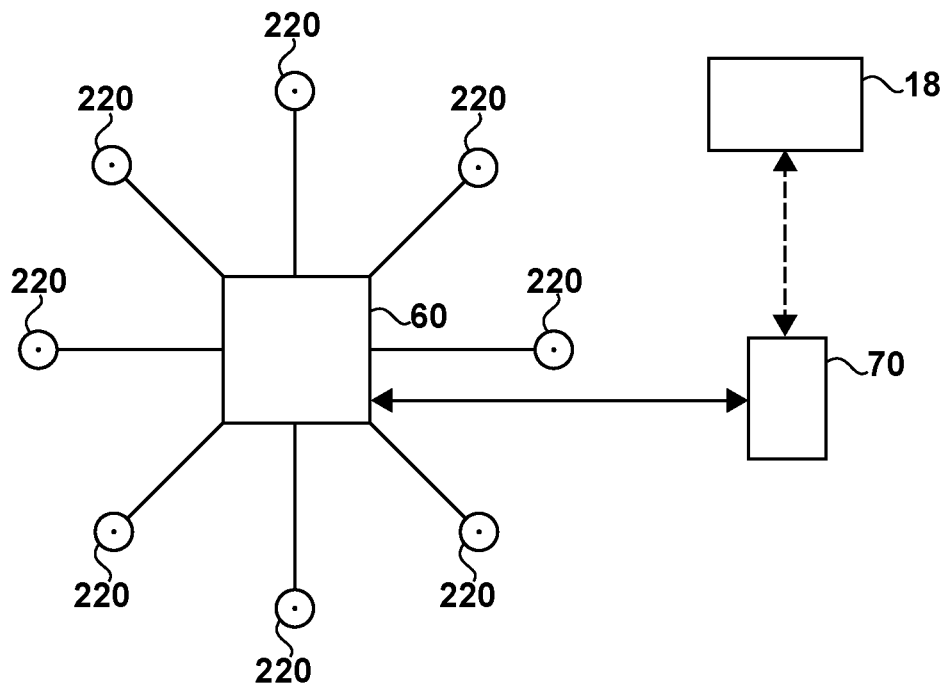
FIG. 13 schematically illustrates some aspects of a non-limiting example of a status interrogation system in the form of a plurality of microphones communicatively coupled to a controller, and to a base station computer via a wireless connection, in accordance with an embodiment of the present invention.

Referring to FIGS. 10 and 13, in some embodiments, inspection vehicle 216 includes a status interrogation system in the form of microphones 220 constructed to detect partial discharge and potential breakdown of insulation within transformer 12. Microphones 220 are communicatively coupled to controller 60 and hence to base station or computer 18 via antenna 70. Partial discharge, e.g., a partial discharge event, is a localized dielectric breakdown of a solid or fluid electrical insulation that may not, at least in the initial stages of failure, be visible. The partial discharge may be intermittent or may be continuous. The continued or repeated occurrence of partial discharge(s) over some duration typically leads to visibly apparent breakdown of insulation and damage to other structures, conductive or otherwise. If caught in the early stages, partial discharge can be addressed by remedial action prior to significant or substantial damage being done to the transformer.

Partial discharge has been found to generate sound, including ultrasonic waves through a solid or liquid filled electrical components, e.g., inside tank or housing 13 filled with dielectric liquid 14. Microphones 220 are constructed to be sensitive in the ultrasonic region associated with partial discharge. In one form, inspection vehicle 216 includes eight (8) microphones 220 disposed about the surface of inspection vehicle 216, equally spaced apart circumferentially from each other. In other embodiments, other orientations and/or numbers of microphones may be employed. Preferably, at least three (3) microphones are employed, although some embodiments may have fewer than three microphones, and as few as one. More preferably, approximately seven (7) to eight (8) microphones are employed, although the number of microphones may vary with the needs of the particular application. In some embodiments, one or more acoustic cameras may be employed in addition to or in place of microphones 220.

System 10 is constructed to triangulate the location of the partial discharge. For example, in order to inspect transformer 12 for the occurrence of partial discharge event, a high voltage may be supplied to transformer 12, such as a normal or a peak operating voltage, but at low current, while inspection vehicle 216 is deployed within tank or housing 13, with microphones 220 immersed within dielectric liquid 14. The high voltage is selected to be representative of actual operating voltage so as to simulate normal operating conditions and to stimulate partial discharge at sites which would otherwise experience the partial discharge during normal operating conditions, whereas the reduced current reduces the damage caused by the partial discharges, and reduces the likelihood of damage to inspection vehicle 216. While the voltage is supplied to transformer 12, inspection vehicle 216 is directed past various portions of transformer 12, while "listening" for partial discharges using microphones 220. In some embodiments, the "listening" may be performed while inspection vehicle 216 is in transit, whereas in other embodiments, inspection vehicle 216 may be paused at desired locations to listen for partial discharges. Once heard, the location of the partial discharge is triangulated, e.g., based on the timing of the partial discharge induced sound waves reaching the locations of the different microphones 220 spaced apart around the circumference of inspection vehicle 216 (phase offset of the received signal as between the different microphones 220), as well as based on the amplitude difference as between the different microphones. In one form, the triangulation calculations are performed by controller 60. In other embodiments, some or all of the microphone data may be wirelessly transmitted to computer 18, and the triangulation calculations may be performed by computer 18 in addition to or in place of controller 60. In some embodiments, only the triangulation results may be transmitted wirelessly to computer 18. Once the location of the partial discharge(s) have been determined, inspection vehicle 216 may be maneuvered adjacent to the location of the partial discharge, and a single microphone 220 may be employed to confirm the exact location of the partial discharge if desired. Once adjacent the partial discharge camera 48 and or one or more other status interrogation systems described herein may be employed to more closely observe or inspect the site for any damage or other physical signs of the partial discharge, e.g., in order to help decide upon remedial action. The power supplied to transformer 12 may be terminated, and then ultrasound sensor 218 may be employed to verify the thickness of insulation at the partial discharge site, or confirm other structural thickness parameters, or the presence and thickness of sediment that may be a contributing cause for the partial discharge.

Figure 14:
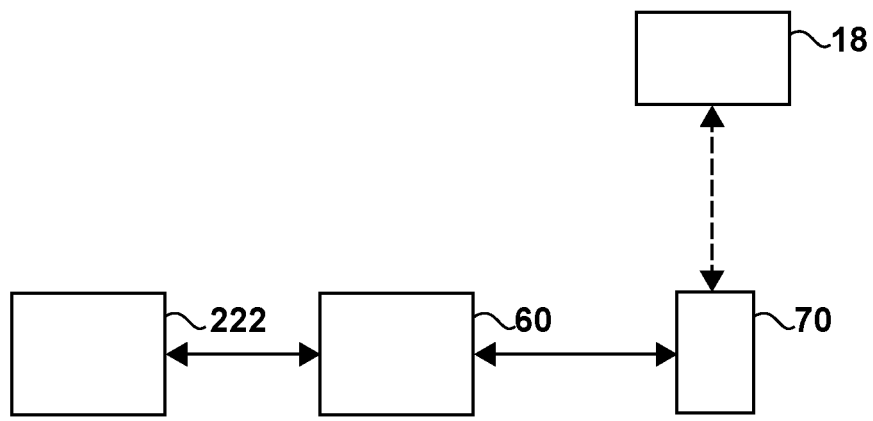
FIG. 14 schematically illustrates some aspects of a non-limiting example of a status interrogation system in the form of a magnetometer communicatively coupled to a controller, and to a base station computer via a wireless connection, in accordance with an embodiment of the present invention.
Figure 15:
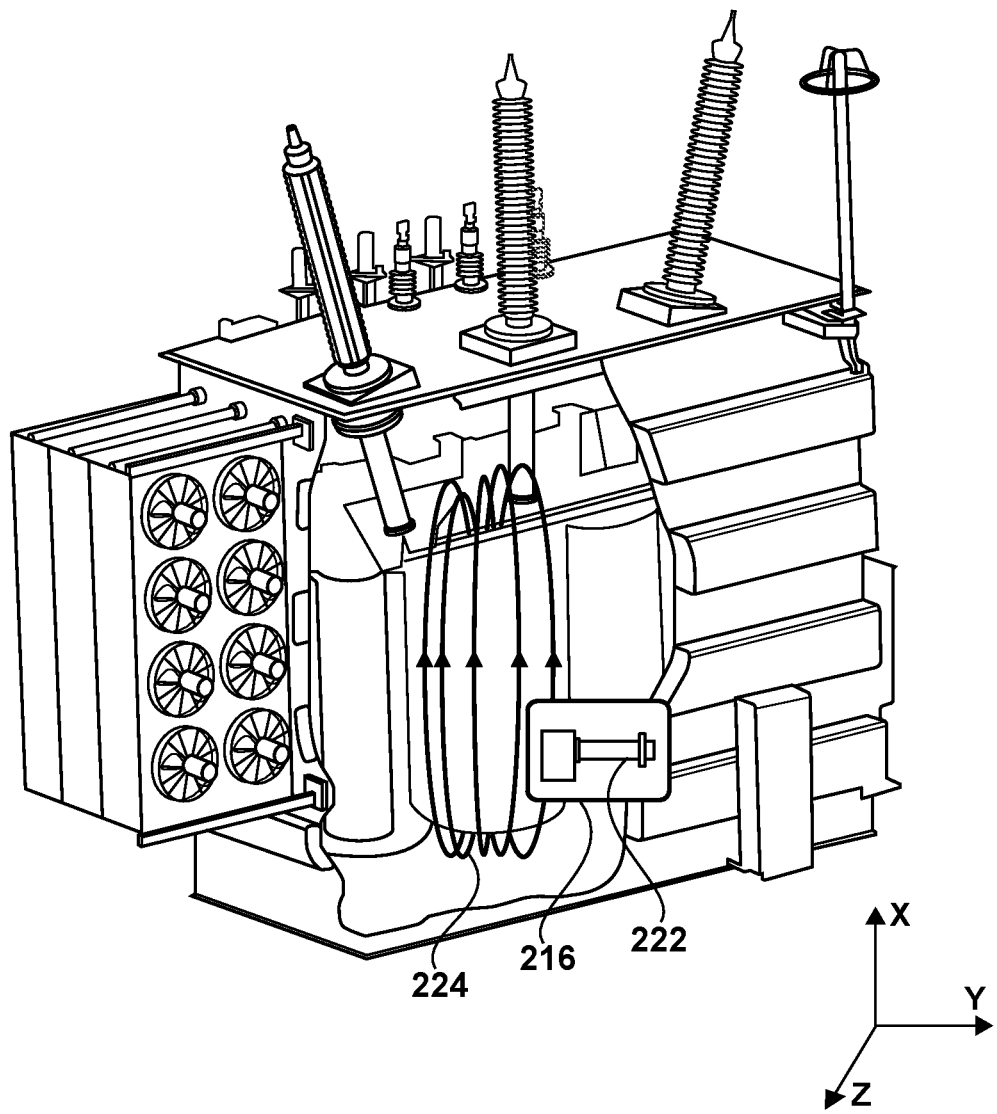
FIG. 15 schematically illustrates some aspects of a non-limiting example of the magnetometer of FIG. 14 detecting magnetic field strength in three axes in accordance an embodiment of the present invention.

Referring to FIGS. 10, 14 and 15, in some embodiments, inspection vehicle 216 includes a status interrogation system in the form a magnetometer 222 (illustrated schematically). Magnetometer 222 is disposed inside of the nonmetallic inspection vehicle 216. In one form, magnetometer 222 is a multiaxis magnetometer. In other embodiments, magnetometer 222 may take other forms. In one form, magnetometer 222 is operative to sense magnetic field lines 224 along X, Y and Z axes, e.g., the X, Y and Z axes illustrated in FIG. 15, and to detect variations in the magnetic field generated by transformer 12. In one form, magnetometer 222 is an orientation independent magnetometer, operative to obtain orientation independent measurement of magnetic fields within tank or housing 13, e.g., emanating from transformer 12. The sampling rate of magnetometer 222 may vary with the needs of the application. Measurement of the magnetic field, coupled with location information provided by inspection vehicle 216 can allow users to form a spatial map of the magnetic field profile within tank or housing 13 and transformer 12, e.g., by wirelessly transmitting the sensed magnetic field data to computer 18 and combining the data with a computer-aided design model of transformer 12 to form the spatial map. Any anomalous magnetic field measurements can be used to trigger an alert, potentially preventing damage or further damage within transformer 12. Magnetometer 222 is coupled to controller 60 and to base station computer 18 via antenna 70. Controller 60 is operative to direct magnetometer 222 to obtain magnetic field data at a desired sample rate. In some embodiments, controller 60 is operative to wirelessly transmit via antenna 70 the magnetic field information to computer 18, which in some embodiments creates a spatial map of the magnetic field profile for visual comparison against a standard or baseline map. In other embodiments, analysis of the magnetic flux lines measured by magnetometer may be performed in other manners.

Figure 16:
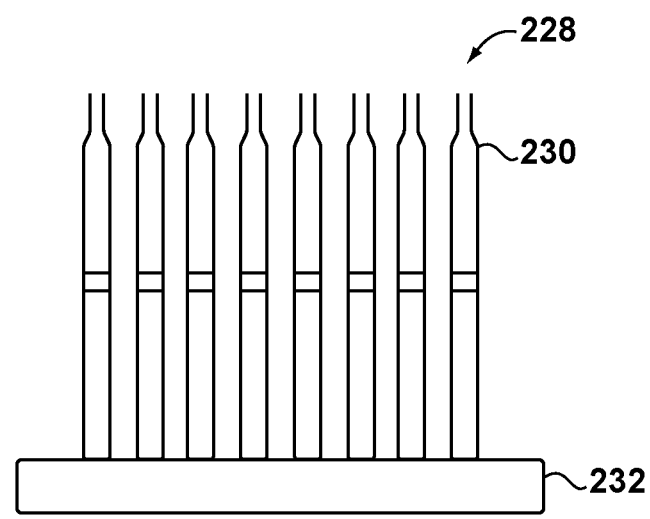
FIG. 16 schematically illustrates some aspects of a non-limiting example of a status interrogation system in the form of an aliquot collection system in accordance an embodiment of the present invention.
Figure 17:
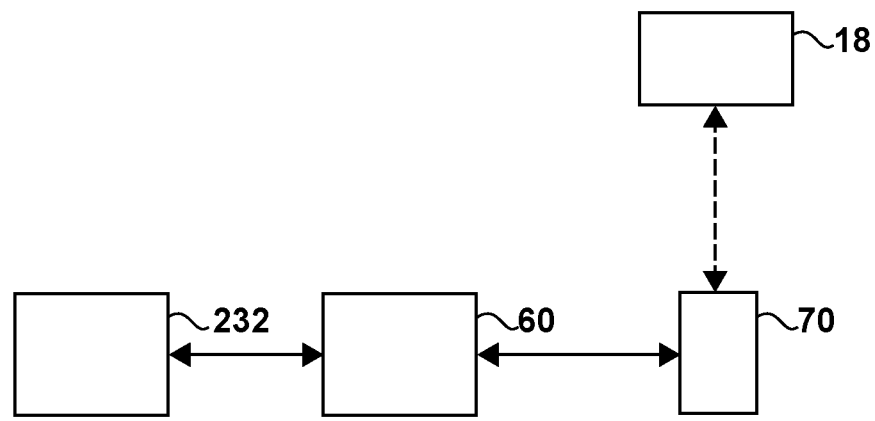
FIG. 17 schematically illustrates some aspects of a non-limiting example of an aliquot collection system plunger drive mechanism communicatively coupled to a controller, and to a base station computer via a wireless connection, in accordance with an embodiment of the present invention.

Referring to FIGS. 10, 16 and 17, in some embodiments inspection vehicle 216 includes a status interrogation system in the form an aliquot collection system 228. Aliquot collection system 228 includes a compartmentalized bank of aliquot collection syringes 230 and a syringe plunger drive mechanism 232. Plunger drive mechanism 232 is communicatively coupled to controller 60, and hence to base station computer 18 via antenna 70. Plunger drive mechanism is operative to operate the aliquot collection syringes to obtain aliquot samples at desired locations, e.g., at the direction of controller 60 and/or computer 18. Aliquot collection system 228 allows inspection vehicle 216 to collect aliquots from different locations around transformer 12 in tank or housing 13, e.g., samples of dielectric cooling liquid 14. The aliquot samples obtained may be analyzed subsequently after removal of the aliquot collection syringes from inspection vehicle 216, allowing the use of sophisticated lab and analysis equipment that, for example, may not be locally available.

In some embodiments, sampling at different heights within tank or housing 13 and transformer 12 may aid in the analysis of particulate/sludge sedimentation. Guidance of inspection vehicle to obtain the aliquot samples may be performed manually or in conjunction with a computer aided design model of tank or housing 13 and transformer 12, allowing collection at desired locations. In one form, aliquot collection syringes 230 are clean, gas-tight and moisture-free syringes, which may prevent contamination of samples once taken. In some embodiments, aliquot collection syringes 230 may be disposable. The type and nature of aliquot collection syringes 230 may vary with the needs of the application. Different forms or types of analytics may be employed, e.g., at an external laboratory, which may aid in assessing transformer health and in assessing the severity of various problems. For example, paper (cellulose) insulation deterioration may be locally assessed in different locations around tank or housing 13 based on the use of the aliquot samples. In addition, liquid insulation overheating problems can be examined, and the level of severity can be estimated based on the use of the aliquot samples. As another example, suspected corona detection can be linked to its location of discharge, for example, if one or more aliquot samples indicates unusually elevated hydrogen levels. Dielectric breakdown tests, interfacial tension and neutralization numbers tests, among others, may be performed on the aliquot samples to indicated the presence of water, cellulose fibers or other particulate contaminants, e.g., which are known to vary at different depths. Also, localized aliquot collection can aid in locating arcing problems when used in conjunction with metals-in-oil analysis.

Figure 18:
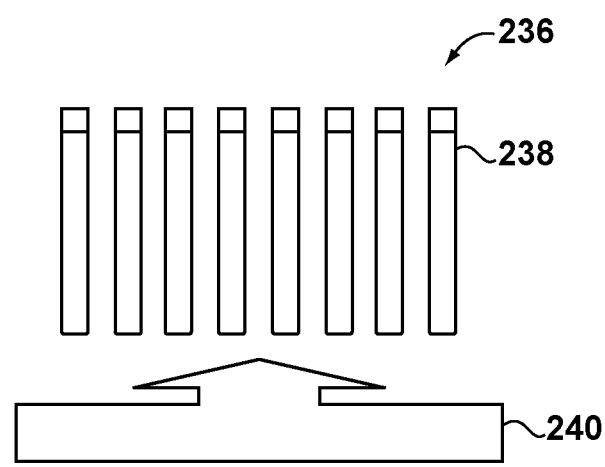
FIG. 18 schematically illustrates some aspects of a non-limiting example of a status interrogation system in the form of mechanical sampling system in accordance an embodiment of the present invention.
Figure 19:
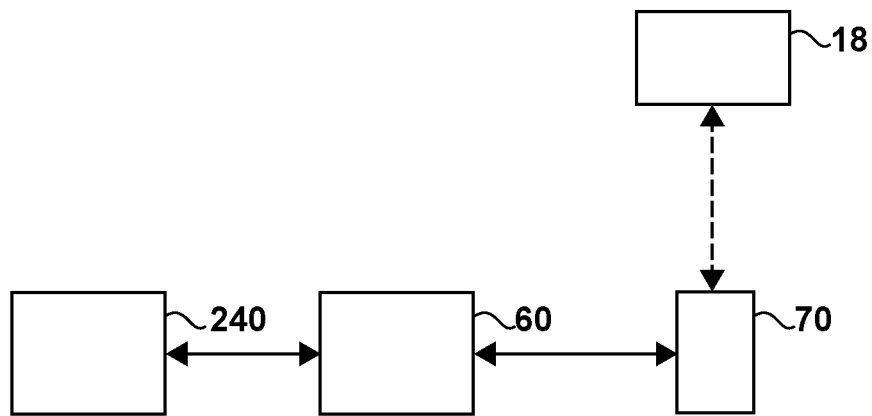
FIG. 19 schematically illustrates some aspects of a non-limiting example of a mechanical sample collection mechanism communicatively coupled to a controller, and to a base station computer via a wireless connection, in accordance with an embodiment of the present invention.

Referring to FIGS. 10, 18 and 19, in some embodiments, inspection vehicle 216 includes a status interrogation system in the form a mechanical sampling system 236. Mechanical sampling system 236 is operative to extract mechanical samples from desired locations within tank or housing 13 and around transformer 12, and store the samples within sample collection bottles 238. Mechanical sampling system 236 includes a sample collection mechanism 240 schematically illustrated in FIG. 18, which is operative to obtain samples, e.g., scrapings or scooping, from desired locations or features of transformer 12 or otherwise within tank or housing 13, for example, grit and sediment samples from the bottom of tank or housing 13, portions of insulation material, carbonization, coking, corrosion or other materials that may warrant further investigation. Sample collection mechanism 240 is communicatively coupled to controller 60, and hence to base station computer 18 via antenna 70. In one form, sample collection mechanism 240 is operative to perform mechanical sampling under the direction of computer 18, e.g., based on user input. In other embodiments, sample collection mechanism 240 is operative to perform mechanical sampling under the direction of controller 60 in addition to the direction of computer 18.

Figure 20:
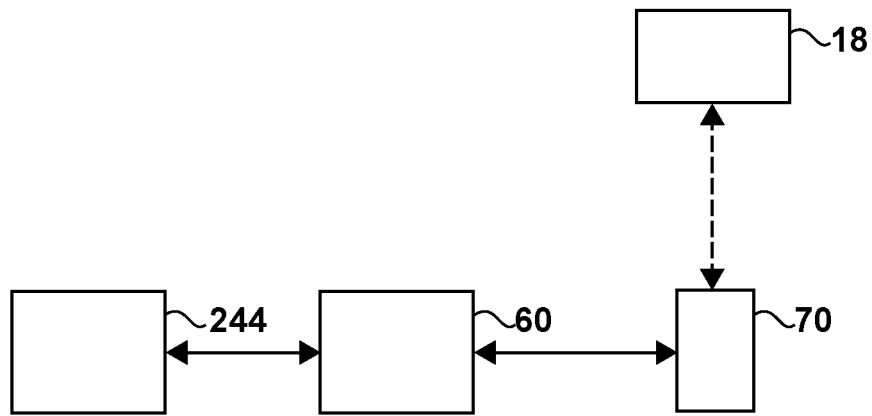
FIG. 20 schematically illustrates some aspects of a non-limiting example of a status interrogation system in the form of a chemical sensor communicatively coupled to a controller, and to a base station computer via a wireless connection, in accordance with an embodiment of the present invention.

Referring to FIGS. 10 and 20, in some embodiments, inspection vehicle 216 includes a status interrogation system in the form a high sample rate chemical sensor 244. Chemical sensor 244 is operative to chemically analyze dielectric cooling liquid 14. In one form, chemical sensor 244 is operative to sense dissolved gaseous species, for example and without limitation, hydrogen, carbon dioxide and/or carbon monoxide. In other embodiments, chemical sensor 244 may be operative to sense other dissolved gas species. In some embodiments, chemical sensor 244 is also or alternatively operative to test for moisture level or other contaminant levels. In some embodiments, a plurality of chemical sensors 244 may be employed, e.g., to test for different contaminant species. Chemical sensor 244 may be, for example, an optical sensor, an optical fiber sensor, or any other chemical sensor type.

Chemical sensor 244 is communicatively coupled to controller 60, and hence to base station computer 18 via antenna 70. Inspection vehicle 216 is operative to wirelessly transmit chemical sensor 244 output to computer 18 via antenna 70. In one form, chemical sensor 244 is operative to test or sense for contaminants in cooling liquid 14 under the direction of computer 18, e.g., based on user input. In some embodiments, chemical sensor 244 may also or alternatively be operative to test or sense for contaminants automatically based on the location of inspection vehicle 216, e.g., under the direction of controller 60 and/or computer 18 with the aid of a computer-aided design model of transformer 12 and tank or housing 13. If a significant deviation from an expected sensor reading is obtained at a particular location, inspection vehicle 216 may be operated to perform more minute inspections around this location using chemical sensor 244 to "home in" on the source of the contamination, after which additional inspection procedures may be performed using camera 48 and/or other status interrogation systems, e.g., such as those disclosed herein. In addition, subsequent inspections using chemical sensor 244 may be performed, e.g., over the course of time. The sensor readings for each inspection may be stored in a memory, e.g., storage device 68 or within computer 18 to record the changes in sensor readings over time. In some embodiments, controller 60 and/or computer 18 may send system alerts indicating abnormal readings, which in some embodiments may include the locations at which the abnormal readings were found. In some embodiments, a location-based mapping of regions within tank or housing 13 that have shown abnormal sensor reading may be generated, which may provide valuable information for use in determining the timing for the next transformer maintenance.

Figure 21:
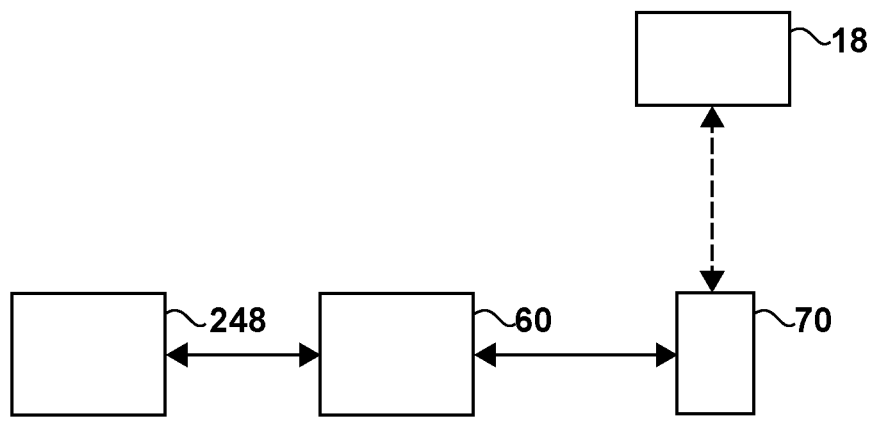
FIG. 21 schematically illustrates some aspects of a non-limiting example of a status interrogation system in the form of an infrared thermometry sensor communicatively coupled to a controller, and to a base station computer via a wireless connection, in accordance with an embodiment of the present invention.

Referring to FIGS. 10 and 21, in some embodiments, inspection vehicle 216 includes a status interrogation system in the form an infrared sensor 248, e.g., an infrared thermometry sensor. Infrared sensor 248 is operative to sense the temperature within tank or housing 13, e.g., the temperature of transformer 12 and/or dielectric cooling liquid 14, at desired locations within tank or housing 13. Infrared sensor 248 is communicatively coupled to controller 60, and hence to base station computer 18 via antenna 70. Inspection vehicle 216 is operative to wirelessly transmit infrared sensor 248 data to computer 18 via antenna 70. In one form, infrared sensor 248 is operative to sense temperature, e.g., of cooling liquid 14, under the direction of computer 18, e.g., based on user input. In some embodiments, infrared sensor 248 may also or alternatively be operative to sense temperature automatically based on the location of inspection vehicle 216, e.g., under the direction of controller 60 and/or computer 18 with the aid of a computer-aided design model of transformer 12 and tank or housing 13.

In a particular form of operation, inspection vehicle 216 is operative to perform infrared thermometry mapping within tank or housing 13 using infrared sensor 248. For example, inspection vehicle 216 may be maneuvered to desired locations, and the temperature sensed using infrared sensor 248. The sensor readings for each inspection may be stored in a memory, e.g., storage device 68 or within computer 18, and in some embodiments may be used to generate a heat profile within transformer 12 and tank or housing 13, allowing monitoring of excessive heating and fluctuations in heat profile that can lead to oil decomposition or degradation of paper insulation. Storage device 68 and/or computer 18 may record the changes in sensor readings over time. A heat map may thus be generated in some embodiments. Variation in the heat map over time may be used to provide an informative analysis of transformer health, particularly when used in conjunction with data from other status interrogation systems, e.g., described herein, such as aliquot collection system 228, mechanical sampling system 238 and chemical sensor 244.

Although embodiments have been described wherein computer 18 functions as a base station controller and remotely and wirelessly directs the movement and actions of inspection vehicle 216 in some embodiments, and/or directs the actions of the status interrogation systems in some embodiments, it will be understood that in other embodiments, inspection vehicle 216 is autonomously guided using controller 60, for example, based on waypoints or other data stored in storage device 68, e.g., a computer-aided design model of transformer 12 and tank or housing 13, and/or that the actions of the status interrogation systems are autonomously operated and controlled by controller 60, e.g., based on the waypoint or other data stored in storage device 68.

Embodiments of the present invention include an inspection system for inspecting a machine, comprising: an inspection vehicle constructed for wireless operation while submersed in a dielectric liquid medium, wherein the inspection vehicle is self-propelled; a controller operative to direct activities of the inspection vehicle; and a plurality of status interrogation systems disposed on the inspection vehicle, wherein the plurality of status interrogation systems are operative to capture inspection data regarding a plurality of inspection procedures performed on the machine.

In a refinement, the inspection system further comprises a base station, wherein the controller is coupled to at least one of the status interrogation systems and operative to wirelessly transmit the captured data to the base station.

In another refinement, the plurality of status interrogation systems includes an ultrasound sensor operative to measure a thickness.

In yet another refinement, the plurality of status interrogation systems includes a microphone operative to sense sound waves associated with a partial discharge.

In still another refinement, the microphone is a plurality of microphones.

In yet still another refinement, the controller is coupled to the plurality of microphones; and the controller is operative to triangulate a location of the partial discharge; or the system further comprises a base station, wherein the controller is operative to wirelessly transmit captured data to the base station, and wherein the base station is operative to triangulate the location of the partial discharge.

In a further refinement, the plurality of status interrogation systems includes a magnetometer operative to quantify a magnetic field of the machine.

In a yet further refinement, the magnetometer is a multi-axis magnetometer.

In a still further refinement, the plurality of status interrogation systems includes an aliquot collection system operative to collect aliquot samples of the dielectric liquid medium.

In a yet still further refinement, the plurality of status interrogation systems includes a mechanical sampling system operative to mechanically obtain samples within the machine.

In another further refinement, the plurality of status interrogation systems includes a chemical sensor operative to sense contaminants in the dielectric liquid medium.

In yet another further refinement, the plurality of status interrogation systems includes an infrared sensor operative to sense a temperature.

In still another further refinement, the controller is a part of the inspection vehicle and operative to autonomously operate the inspection vehicle and/or the plurality of status interrogation systems.

In yet still another further refinement, the inspection system further comprises a base station operative to wirelessly direct the activities of the inspection vehicle, wherein the controller is a part of the base station.

Embodiments of the present invention include a method for performing an inspection of a machine, comprising: providing a plurality of status interrogation systems on an inspection vehicle, wherein the plurality of status interrogation systems are operative to capture inspection data regarding a plurality of inspection procedures to be performed on the machine; immersing the inspection vehicle within a dielectric liquid medium inside a housing of the machine; operating a base station to wirelessly direct a maneuvering of the inspection vehicle within the machine and to wirelessly direct the plurality of inspection procedures of the inspection vehicle using the plurality of status interrogation systems while immersed within the dielectric medium.

In a refinement, the plurality of status interrogation systems includes an ultrasound sensor, further comprising measuring a thickness while the inspection vehicle is immersed within the dielectric liquid medium using the ultrasound sensor.

In another refinement, the plurality of status interrogation systems includes a microphone operative to sense sound waves associated with a partial discharge event, further comprising further comprising determining a location of a partial discharge event within the housing using the microphone while the inspection vehicle is immersed within the dielectric liquid medium.

In yet another refinement, the plurality of status interrogation systems includes a magnetometer, further comprising sensing a magnetic field strength in the machine using the magnetometer while the inspection vehicle is immersed within the dielectric liquid medium.

In still another refinement, the plurality of status interrogation systems includes at least one of: an aliquot collection system operative to collect aliquot samples of the medium while the inspection vehicle is immersed in the dielectric liquid medium; and a mechanical sampling system operative to mechanically collect samples within the machine while the inspection vehicle is immersed within the dielectric liquid medium.

In yet still another refinement, the plurality of status interrogation systems includes a chemical sensor, further comprising sensing for contaminants in the dielectric liquid medium using the chemical sensor while the inspection vehicle is immersed within the dielectric liquid medium.

In a further refinement, the plurality of status interrogation systems includes an infrared thermometry sensor, further comprising sensing a temperature using the infrared thermometry sensor while the inspection vehicle is immersed within the dielectric liquid medium.

Embodiments of the present invention include an inspection system for inspecting a machine, comprising: an inspection vehicle constructed for operation while submersed within a dielectric liquid medium, wherein the inspection vehicle is self-propelled; a base station operative to direct activities of the inspection vehicle; means for communicating between the base station and the inspection vehicle; and a plurality of means for interrogating the status of the machine, wherein the means for interrogating are disposed on the inspection vehicle.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

What is claimed is:

1. An inspection system for inspecting a machine, comprising:
   an inspection vehicle constructed for wireless operation while submersed in a dielectric liquid medium, wherein the inspection vehicle is self-propelled;
   a controller operative to direct activities of the inspection vehicle;
   a plurality of status interrogation systems disposed on the inspection vehicle; and
   a base station operative to wireles sly direct the activities of the inspection, wherein the controller is a part of the base station,
   wherein the plurality of status interrogation systems are operative to capture inspection data regarding a plurality of inspection procedures performed on the machine,
   wherein the plurality of status interrogation systems includes a magnetometer operative to quantify a magnetic field of the machine,
   wherein the magnetometer is a three axis magnetometer and
   wherein the plurality of status interrogation systems includes more than two microphones operative to sense sound waves associated with a partial discharge and that are disposed on the inspection vehicle.

2. The inspection system of claim 1, further comprising a base station, wherein the controller is coupled to at least one of the status interrogation systems and operative to wireles sly transmit the captured data to the base station.

3. The inspection system of claim 1, wherein the plurality of status interrogation systems includes an ultrasound sensor operative to measure a thickness.

4. The inspection system of claim 1, wherein the more than two microphones comprises three microphones that are equally spaced part from each other.

5. The inspection system of claim 4, wherein the controller is coupled to the three microphones; and wherein the controller is operative to triangulate a location of the partial discharge; or further comprising a base station, wherein the controller is operative to wirelessly transmit captured data to the base station, and wherein the base station is operative to triangulate the location of the partial discharge.

6. The inspection system of claim 1, wherein the plurality of status interrogation systems includes an aliquot collection system operative to collect aliquot samples of the dielectric liquid medium.

7. The inspection system of claim 1, wherein the plurality of status interrogation systems includes a mechanical sampling system operative to mechanically obtain samples within the machine.

8. The inspection system of claim 1, wherein the plurality of status interrogation systems includes a chemical sensor operative to sense contaminants in the dielectric liquid medium.

9. The inspection system of claim 1, wherein the plurality of status interrogation systems includes an infrared sensor operative to sense a temperature.

10. The inspection system of claim 1, wherein the controller is a part of the inspection vehicle and operative to autonomously operate the inspection vehicle and/or the plurality of status interrogation systems.

11. A method for performing an inspection of a machine, comprising:
    providing a plurality of status interrogation systems on an inspection vehicle, wherein the plurality of status interrogation systems are operative to capture inspection data regarding a plurality of inspection procedures to be performed on the machine;
    immersing the inspection vehicle within a dielectric liquid medium inside a housing of the machine;

operating a base station to wirelessly direct a maneuvering of the inspection vehicle within the machine and to wirelesly direct the plurality of inspection procedures of the inspection vehicle using the plurality of status interrogation systems while immersed within the dielectric medium, wherein the plurality of status interrogation systems includes a magnetometer, further comprising sensing a magnetic field strength in the machine using the magnetometer while the inspection vehicle is immersed within the dielectric liquid medium, wherein the plurality of status interrogation systems includes an ultrasound sensor, further comprising measuring a transformer wall thickness while the inspection vehicle is immersed within the dielectric liquid medium using the ultrasound sensor, and wherein the plurality of status interrogation systems includes more than two microphones operative to sense sound waves associated with a partial discharge event.

12. The method of claim 11, further comprising determining a location of a partial discharge event within the housing using one microphone of the more than two microphones while the inspection vehicle is immersed within the dielectric liquid medium.

13. The method of any of claim 11, wherein the plurality of status interrogation systems includes at least one of: an aliquot collection system operative to collect aliquot samples of the medium while the inspection vehicle is immersed in the dielectric liquid medium; and a mechanical sampling system operative to mechanically collect samples within the machine while the inspection vehicle is immersed within the dielectric liquid medium.

14. The method of any of claim 11, wherein the plurality of status interrogation systems includes a chemical sensor, further comprising sensing for contaminants in the dielectric liquid medium using the chemical sensor while the inspection vehicle is immersed within the dielectric liquid medium.

15. The method of any of claim 11, wherein the plurality of status interrogation systems includes an infrared thermometry sensor, further comprising sensing a temperature using the infrared thermometry sensor while the inspection vehicle is immersed within the dielectric liquid medium.

16. An inspection system for inspecting a machine, comprising:

an inspection vehicle constructed for operation while submersed within a dielectric liquid medium, wherein the inspection vehicle is self-propelled;

a base station operative to direct activities of the inspection vehicle, wherein the base station comprises a controller operative to direct activities of the inspection vehicle;

means for communicating between the base station and the inspection vehicle; and a plurality of means for interrogating the status of the machine, wherein the means for interrogating are disposed on the inspection vehicle, wherein the plurality of means for interrogating the status of the machine includes more than two microphones operative to sense sound waves associated with a partial discharge event.

* * * * *